United States Patent
Ohzawa

(10) Patent No.: US 8,602,975 B2
(45) Date of Patent: Dec. 10, 2013

(54) OPTICAL ROTARY PROBE

(75) Inventor: Soh Ohzawa, Toyonaka (JP)

(73) Assignee: Konica Minolta Opto, Inc., Tokyo (JP)

( * ) Notice: Subject to any disclaimer, the term of this patent is extended or adjusted under 35 U.S.C. 154(b) by 213 days.

(21) Appl. No.: 13/125,176

(22) PCT Filed: Sep. 10, 2009

(86) PCT No.: PCT/JP2009/065803
§ 371 (c)(1),
(2), (4) Date: Apr. 20, 2011

(87) PCT Pub. No.: WO2010/047190
PCT Pub. Date: Apr. 29, 2010

(65) Prior Publication Data
US 2012/0008898 A1    Jan. 12, 2012

(30) Foreign Application Priority Data
Oct. 20, 2008 (JP) .................. P2008-269491

(51) Int. Cl.
*A61B 1/00* (2006.01)

(52) U.S. Cl.
USPC ........................................ 600/137; 385/902

(58) Field of Classification Search
USPC ........................................ 600/137; 385/902
See application file for complete search history.

(56) References Cited

U.S. PATENT DOCUMENTS

| | | | |
|---|---|---|---|
| 5,321,501 A | 6/1994 | Swanson et al. | |
| 5,459,570 A | 10/1995 | Swanson et al. | |
| 5,872,879 A | 2/1999 | Hamm | |
| 5,949,929 A | 9/1999 | Hamm | |
| 6,546,272 B1* | 4/2003 | MacKinnon et al. | 600/407 |
| 6,692,431 B2* | 2/2004 | Kazakevich | 600/178 |
| 7,324,211 B2 | 1/2008 | Tsujita | |
| 7,589,316 B2* | 9/2009 | Dunki-Jacobs | 250/235 |
| 7,857,758 B2* | 12/2010 | Teramura | 600/182 |
| 2004/0109164 A1* | 6/2004 | Horii et al. | 356/479 |
| 2005/0038322 A1* | 2/2005 | Banik | 600/129 |
| 2005/0143664 A1* | 6/2005 | Chen et al. | 600/478 |
| 2005/0177026 A1* | 8/2005 | Hoeg et al. | 600/173 |

(Continued)

FOREIGN PATENT DOCUMENTS

| | | |
|---|---|---|
| JP | 4-135550 | 5/1992 |
| JP | 6-511312 | 12/1994 |

(Continued)

*Primary Examiner* — Charlie Peng
(74) *Attorney, Agent, or Firm* — Cozen O'Connor

(57) ABSTRACT

There is disclosed a probe (50) for directing light to an object to be measured and receiving light returned from the object to be measured, the probe including: an optical path (21) for transmitting light from a light source (10); a mirror member (52) for reflecting the light transmitted through the optical path (21); and a rotational oscillation mechanism (56) for rotatably oscillating the mirror member (52) and a tip end portion of the optical path (21) about a longitudinal axis of the optical path (21); wherein the rotational oscillation mechanism (56) is adapted to perform the rotational oscillation within a range defined by a torsional elasticity limit of the optical path (21). This configuration can provide an optical rotary probe with a simple structure and with high reliability, which is capable of suppressing optical losses and reflection ghosts.

8 Claims, 3 Drawing Sheets

(56) References Cited

U.S. PATENT DOCUMENTS

| | | |
|---|---|---|
| 2006/0066865 A1 | 3/2006 | Tsujita |
| 2007/0076429 A1 | 4/2007 | Ohkubo |
| 2007/0197874 A1 | 8/2007 | Ishihara |
| 2008/0021487 A1* | 1/2008 | Heisler .................. 606/170 |
| 2008/0188711 A1* | 8/2008 | Eliachar et al. ............ 600/106 |
| 2008/0267562 A1* | 10/2008 | Wang et al. ................ 385/31 |
| 2011/0178409 A1* | 7/2011 | Harris et al. .................. 600/476 |

FOREIGN PATENT DOCUMENTS

| | | |
|---|---|---|
| JP | 2006-095143 | 4/2006 |
| JP | 2007-121257 | 1/2007 |
| JP | 2007-222381 | 9/2007 |
| WO | WO 2006/119173 | 11/2006 |

* cited by examiner

OPTICAL ROTARY PROBE

RELATED APPLICATIONS

This is a U.S. National Phase under 35 U.S.C. §371 of International Application No. PCT/JP2009/065803, filed on Sep. 10, 2009, and claims priority on Japanese application No. 2008-269491, filed on Oct. 20, 2008, the entire content of which is hereby incorporated by reference.

TECHNICAL FIELD

The present invention relates to optical rotary probes, which are suitable for use in, for example, optical coherent tomography (OCT) apparatuses, for directing light toward an object to be measured and receiving light returned from the object to be measured.

BACKGROUND

In recent years, for diagnosing body tissues, optical coherent tomography (OCT) apparatuses which are capable of obtaining optical information about insides of tissues are proposed, as well as imaging apparatuses for obtaining optical information about conditions of the surfaces of such tissues. Optical coherent tomography apparatuses employ techniques for dividing low-coherence light into two parts, further directing one part of the light toward an object to be measured and causing the returned scattering light modified with phase information about the object to interfere with the other part of light, further obtaining the phase information about the object from information about the intensity of the interfering light and, further, imaging the measured portion of the object (See Patent Document 1).

PRIOR ART DOCUMENT [Patent Document]

[PATENT DOCUMENT 1] JP 6-511312 A
[PATENT DOCUMENT 2] JP 2007-222381 A (FIG. 14)
[PATENT DOCUMENT 3] JP 2006-95143 A (FIG. 2)
[PATENT DOCUMENT 4] JP 4-135550 A (FIG. 6)
[PATENT DOCUMENT 5] U.S. Pat. No. 5,872,879 B
[PATENT DOCUMENT 6] U.S. Pat. No. 5,949,929 B

DISCLOSURE OF THE INVENTION

Problem to be Solved by the Invention

When diagnosing fine body tissues such as blood vessels, using optical signals, in general, a bendable thin optical probe which is formed of a fiber or the like can be used for rotational scanning about the axis of the probe to obtain images of inner walls and cross-sections of the blood vessels. In cases of such a rotational-scanning type optical probe, a mechanical break point is conventionally provided in the fiber optical path of the probe, and one side thereof is fixed while the other side is rotated for enabling scanning over the entire periphery with an angle of 360 degrees.

However, a complicated mechanism is needed for suppressing optical losses and reflections around the break point. Further, in cases of obtaining tomography images such as OCTs, it is necessary to accurately suppress variation of the optical path length during rotating around the break point, which leads to an increase cost of the components and degraded reliability of the apparatus.

Patent Documents 2 and 3 disclose rotational scanning in which a fiber probe is mechanically separated from a tip end mirror which can rotate. However, a mirror rotating mechanism must be located at the tip end of the probe, and the positions of the mirror and the fiber end face must be maintained with excellent accuracy, thereby resulting in the enlarged tip end of the probe.

Patent Document 4 discloses that light condensed by a lens is introduced into a rotary fiber probe. However, in order to efficiently introduce light into the rotary probe, it is necessary to accurately adjust both of the rotating position of the probe and the condensing position of the lens. Furthermore, a larger amount of reflection at the incident end face of the probe may cause increased noises.

Patent Documents 5 and 6. disclose that fiber coupling portions are formed as ferrules. However, it is necessary to accurately adjust the axial distance thereof. Furthermore, there is a possibility of fractures due to contact between the end faces, thereby degrading the reliability.

It is an object of the present invention to provide an optical rotary probe with a simple structure and with high reliability, which is capable of suppressing optical losses and reflection ghosts.

Means for Solving the Problem

In order to attain the aforementioned object, according to the present invention, there is provided an optical rotary probe for directing light to an object to be measured and receiving light returned from the object to be measured, the optical rotary probe including: an optical waveguide for transmitting light from a light source; a mirror member for reflecting the light transmitted through the optical waveguide; and a rotational oscillation mechanism for rotatably oscillating the mirror member and a tip end portion of the optical waveguide about a longitudinal axis of the optical waveguide; wherein the rotational oscillation mechanism is adapted to perform the rotational oscillation within a range defined by a torsional elasticity limit of the optical waveguide.

In the present invention, a fixing holding member for restricting the torsional range is preferably provided halfway through the optical waveguide.

In the present invention, a sag is preferably provided in the torsionally oscillating portion of the optical waveguide.

In the present invention, it is preferable that measurement is performed within a constant speed interval of the torsional oscillation while no measurement is performed within a non-constant speed interval.

In the present invention, a second optical waveguide is preferably further provided for transmitting return light from the object to be measured.

In the present invention, the respective optical waveguides are preferably housed in a single bendable flexible member.

In the present invention, the rotational oscillation mechanism is preferably adapted to integrally rotatably oscillate the respective optical waveguides with respect to the bendable flexible member.

Effect of the Invention

According to the present invention, the mirror member and the tip end portion of the optical waveguide are rotated and oscillated within a range defined by a torsional elasticity limit of the optical waveguide, which lead to eliminate the necessity of providing a mechanical break point halfway through the optical waveguide. This can suppress optical losses and reflection ghosts induced by such a mechanical break point, thereby achieving rotational scanning with higher reliability and lower cost.

EXPLANATORY NOTE

Figure 1:
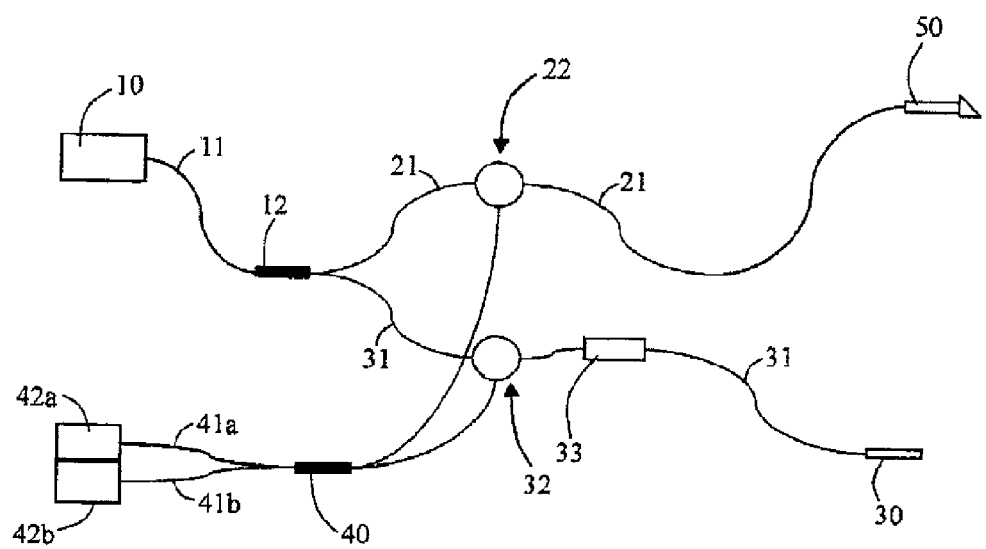
FIG. 1 is a structural view illustrating an example of an optical tomography measurement apparatus to which the present invention is applicable.

10 Light source
11, 21, 31, 41a and 41b Optical path
12, 40 Coupler
21a Torsion portion
21b Sag portion
22, 32 Circulator
25 Fixing holding member
30 Reference mirror
33 Attenuator
42a, 42b Differential detector
50 Probe
51 Objective lens
52 Mirror member
55 Rotational holding member
56 Rotational oscillation mechanism
57 Sheath
58 Sheath holding member Best Embodiment for Carrying out the Invention (First Embodiment)

FIG. 1 is a structural view illustrating an example of an optical tomography measurement apparatus to which the present invention is applicable. The optical tomography measurement apparatus, which is constituted as a Michelson interferometer with a low-coherence light source, includes a light source 10, a coupler 12, circulators 22 and 32, an attenuator 33, a probe 50, a reference mirror 30, a coupler 40, differential detectors 42a and 42b, and a plurality of optical paths 11, 21, 31, 41a and 41b. The optical paths 11, 21, 31, 41a and 41b include a flexible single-mode optical fiber.

The light source 10, which is constituted by an SLD or the like, is adapted to generate low-coherence light with, for example, a center wavelength of 1.3 micrometers (μm) and an oscillation spectrum width of about 50 nm. The light from the light source 10 passes through the optical path 11 and reaches the coupler 12.

The coupler 12, which is constituted by an optical fiber coupler, a beam splitter or the like, has a function of an optical splitting means for splitting the light from the optical path 11 toward the optical paths 21 and 31 with a predetermined ratio.

Sample light split by the coupler 12 passes through the optical path 21 and the circulator 22 and reaches the probe 50. The probe 50 directs the sample light to an object to be measured. The sample return light, which has been reflected according to the internal structure of the object to be measured, enters the probe 50 again, and then passes backward through the optical path 21 and the circulator 22 and then reaches the coupler 40.

Reference light split by the coupler 12 passes through the optical path 31, the circulator 32 and the attenuator 33 and reaches the reference mirror 30. The reference return light, which is reflected by the reference mirror 30, passes backward through the optical path 31, the attenuator 33 and the circulator 32 and then reaches the coupler 40.

The sample return light and the reference return light having passed backward through the optical paths 21 and 31, respectively, are mixed with each other at the coupler 40 to generate interference light. The coupler 40, which is constituted by an optical fiber coupler, a beam splitter or the like, has a function of an optical interference means for causing the light passing backward through the optical paths 21 and 31 to interfere with each other. The interference light passes through the optical paths 41a and 41b and reaches the differential detectors 42a and 42b. The differential detectors 42a and 42b can output a difference between two interference signals.

The signals from the differential detectors 42a and 42b are subjected to various noise elimination and filtering processes, and then converted into digital signals, which are stored in a signal processing device, such as a personal computer. The signal processing device builds up optical tomography images using the stored data according to an optical tomography measurement as described later.

Optical tomography measurements are generally classified into time domain OCTs (TD-OCTs) and Fourier domain OCTs (FD-OCTs). Further, Fourier domain OCTs are classified into swept-source type OCTs (SS-OCTs) and spectral-domain OCTs (SD-OCTs). Time domain OCTs modulate the phase of light according to scan signals using an optical phase modulation device provided in one or both of the optical paths 21 and 31. Swept-source type OCTs modulate the wavelength of light according to scan signals using a wavelength-variable light source, i.e., the light source 10. Spectral-domain OCTs perform spectrometry using a diffraction grating on interference light generated by sample return light and reference return light to measure the spectrum resulted from the spectrometry using a liner image sensor.

The present invention is applicable to any of the aforementioned methods, but can be preferably applied to swept-source type OCTs or spectral-domain OCTs, since it is possible to eliminate the necessity of a mechanism for changing the optical path length with time being located in the reference optical path.

In this embodiment, interference signals generated by sample return light and reference return light are differentially detected. Thus, signals generated by interfering the light from the sample optical path with the light from the reference optical path at the coupler 40 can be increased in intensity due to differential detection of signals having opposite phases. On the other hand, for example, interference signals resulting from ghosts caused by optical surfaces of prisms which are placed in the sample optical path are simply split into the same phase by the coupler 40, which can reduce noise signals through the differential detection, thereby resulting in better optical tomography images.

Further, sample light and reference light are transmitted through the respective different optical fibers, which enables the attenuator 33 to be inserted only in the reference optical path 31. Thus, the amount of reference return light can be easily controlled, thereby achieving optimum adjustment of the amount of light for interference. Further, since sample light and reference light pass through the respective different optical paths, it is possible to eliminate ghost light induced in the sample optical path.

Figure 2:
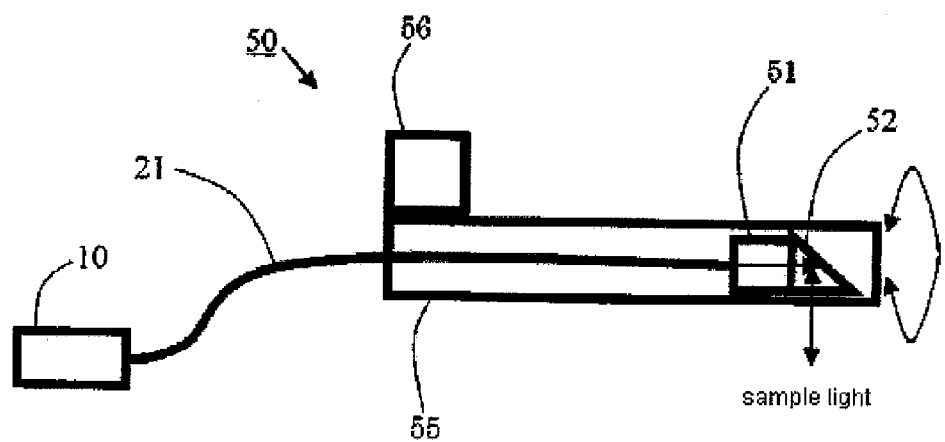
FIG. 2 is a structural view illustrating a probe according to a first embodiment.

FIG. 2 is a structural view illustrating the probe according to the first embodiment. The probe 50 includes the optical path 21 formed of an optical fiber, an objective lens 51, a mirror member 52, a rotational holding member 55, a rotational oscillation mechanism 56.

The objective lens 51, which is constituted of, for example, a gradient index (GRIN) lens or a curved-surface lens, is fixed so that the tip end of the optical path 21 is abutted on the incidence surface of the objective lens 51. The mirror member 52, which is constituted of, for example, a reflection prism, is fixed so that the exit surface of the objective lens 51 is abutted on the incidence surface of the mirror member 52.

The sample light from the light source 10 passes through the optical path 21, and is condensed by the objective lens 51, and then is reflected by the mirror member 52 to spotlight the object to be measured. The sample return light reflected according to the internal structure of the object enters the mirror member 52 again, and then passes backward through the objective lens 51 and the optical path 21, and then passes through the circulator 22 as illustrated in FIG. 1 and returns to the coupler 40.

The rotational holding member 55 is formed of a hollow cylindrical member that can be made of a hard material, such as metal or plastic, or a bendable and flexible material. The objective lens 51 and the mirror member 52 are secured to the inside of the tip end of the rotational holding member 55. The portion thereof facing to the exit surface of the objective lens 51 is provided with an opening or a window made of a transparent material, through which light can pass. The rotational holding member 55 is supported rotatably about the longitudinal axis of the cylinder.

The rotational oscillation mechanism 56, which is constituted of a motor or the like, is adapted to rotatably oscillate the objective lens 51 and the mirror member 52 about the longitudinal axis of the optical path 21 through the rotational holding member 55, so that the object surrounding the rotational holding member 55 can be cylindrically scanned. In this case, the rotational oscillation can be performed within a range defined by a torsional elasticity limit of the optical path 21, which lead to eliminate the necessity of providing a mechanical break point halfway through the optical waveguide, as in conventional structures. Therefore, it is possible to suppress optical losses and reflection ghosts caused by such a mechanical break point, thereby achieving rotational scanning with higher reliability and lower cost.

Further, since the optical path 21 is constituted of an optical fiber, it is possible to reduce optical transmission losses in the optical path 21. Furthermore, since the optical path 21 can be freely bent, it is suitable for applications to endoscopes and vascular catheters.

In processing the interference signals generated by the sample return light and the reference return light, it is preferable that measurement is performed within a constant speed interval of the torsional oscillation while no measurement is performed within a non-constant speed interval. This can reduce the amount of image processing calculations required for building up optical topography images, thereby obtaining the images more quickly and reducing the data storage area required for image processing.

In this regard, it is preferable to provide a detector for detecting the rotational angles of the rotating members including the rotational holding member 55 and the rotational oscillation mechanism 56, thereby determining the constant speed interval of the torsional oscillation.

Further, even when the rotational speed is varied, it is possible to output images while correcting any deviation of measuring positions based on rotational position information, thereby reducing image distortion due to the variation of the rotational speed.

(Second Embodiment)

Figure 3:
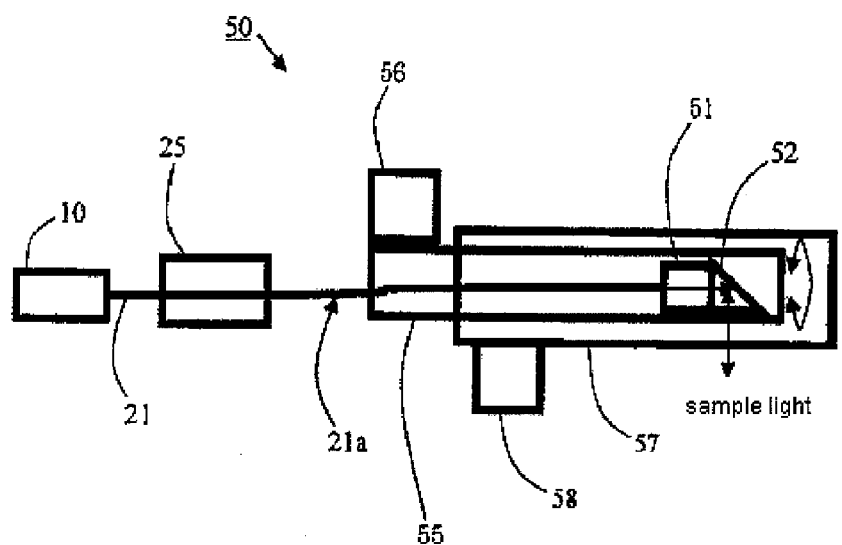
FIG. 3 is a structural view illustrating a probe according to a second embodiment.

FIG. 3 is a structural view illustrating a probe according to the second embodiment. The probe 50 includes an optical path 21 formed of an optical fiber, an objective lens 51, a mirror member 52, a rotational holding member 55, a rotational oscillation mechanism 56, a sheath 57, a sheath holding member 58. The structure and operation for rotational scanning of sample light are the same as those according to the first embodiment in FIG. 2 and, therefore, will not be described redundantly.

The sheath 57, which is formed of a hollow cylindrical member that can be made of a hard material, such as metal or plastic, or a bendable and flexible material, supports the rotational holding member 55 inside thereof so that it can be rotated. The sheath holding member 58 fixes the sheath 57 for restricting the rotational movement of the sheath 57.

In this embodiment, a fixing holding member 25 is installed halfway through the optical path 21 for restricting the torsional range thereof. Installation of the fixing holding member 25 can restrict the area of the torsion portion 21a which is torsionally oscillated, out of the entire optical path 21. This reduces variation of the elasticity limit due to bending or attitude change of the optical path 21, thereby making it easy to set a maximum value of the amount of torsional rotation.

(Third Embodiment)

Figure 4:
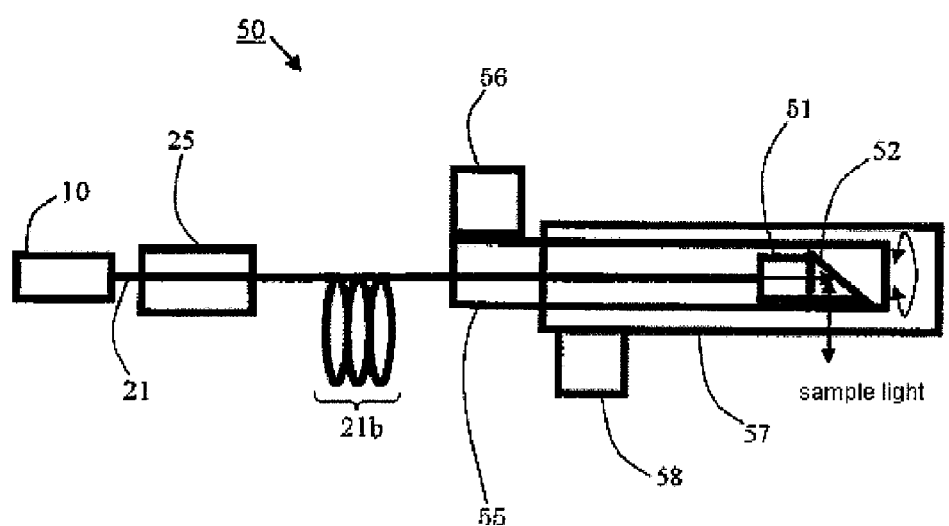
FIG. 4 is a structural view illustrating a probe according to a third embodiment.

FIG. 4 is a structural view illustrating a probe according to the third embodiment. The probe 50 includes an optical path 21 formed of an optical fiber, an objective lens 51, a mirror member 52, a rotational holding member 55, a rotational oscillation mechanism 56, a sheath 57, a sheath holding member 58. The structure and operation for rotational scanning of sample light are the same as those according to the first embodiment in FIG. 2 and, therefore, will not be described redundantly. Further, the structure of the sheath 57 is the same as that of the second embodiment in FIG. 3 and, therefore, will not be described redundantly.

In this embodiment, similarly to the second embodiment, a fixing holding member 25 is installed halfway through the optical path 21 for restricting the torsional range thereof. Installation of the fixing holding member 25 can restrict the area of the torsion portion 21a which is torsionally oscillated, out of the entire optical path 21. This reduces variation of the elasticity limit due to bending or attitude change of the optical path 21, thereby making it easy to set a maximum value of the amount of torsional rotation.

Further, it is preferable to provide a sag portion 21b halfway through the optical path 21. By doing this, it is possible to increase the amount of rotation within an elasticity limit against torsional oscillation, thereby increasing the rotational speed and performing plural rotations. Further, the sag portion 21b is preferably made to have a coil shape as illustrated in FIG. 4. Thus, the permissible amount of torsional rotation can be increased with a smaller space, thereby downsizing the probe 50.

(Fourth Embodiment)

The present invention is also applicable to probes for fluorometric determinations, spectroscopic determinations and confocal scanning, as well as to OCT probes. In cases of these probes, a total of two optical fibers are required, one being a source light guiding optical fiber for guiding light from a light source for illuminating an object to be measured, another being a measuring light guiding optical fiber for guiding fluorescence or scattering light from the illuminated object toward an optical detector or a spectroscope, therefore, it is difficult in general to perform rotational scanning over measuring areas.

In this embodiment, the two optical fibers can be torsionally oscillated within the elasticity limit thereof, thereby obtaining rotational scanning images, without taking any specific measure for connection portion between the rotating portion and the fixed portion.

Figure 5:
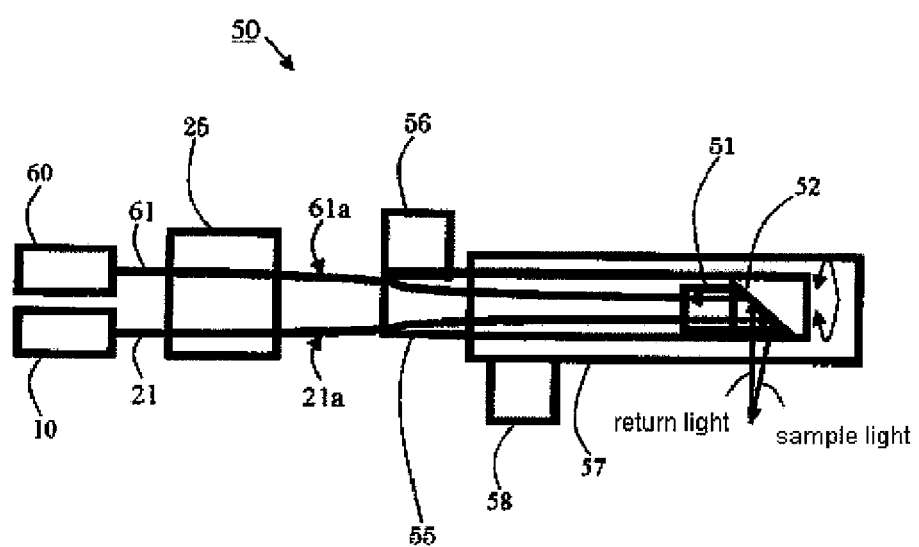
FIG. 5 is a structural view illustrating a probe according to a fourth embodiment.

FIG. 5 is a structural view illustrating a probe according to the fourth embodiment. The probe 50 includes two optical paths 21 and 61 formed of optical fibers, an objective lens 51, a mirror member 52, a rotational holding member 55, a rotational oscillation mechanism 56, a sheath 57, a sheath holding member 58. The structure and operation for rotational scanning of sample light are the same as those according to the first embodiment in FIG. 2 and, therefore, will not be described redundantly.

The sample light from the light source 10 passes through the optical path 21 and is condensed by the objective lens 51, and then is reflected by the mirror member 52 to spotlight the object to be measured. Reflected light or fluorescent light generated by spot irradiation will become sample return light, which enters the mirror member 52 again, and then passes through the objective lens 51 and the second optical path 61, and then is received by an optical detector 60. The detected signal is supplied to a signal processing device such as a computer, which performs measurement for changes of light intensity, spectroscopic spectra and the like.

As described above, sample light and sample return light are transmitted through the respective different optical fibers 21 and 61, which enables an attenuator to be inserted only in one of the optical paths. Thus, the amount of light for the respective optical paths can be easily and independently controlled, thereby achieving optimum adjustment of the amount of light for interference. Further, since sample light and reference light pass through the respective different optical paths, it is possible to eliminate ghost light induced in the sample optical path.

The rotational holding member 55 integrally houses the two optical paths 21 and 61. The objective lens 51 and the mirror member 52 are secured to the inside of the tip end of the rotational holding member 55.

The rotational oscillation mechanism 56, which is constituted of a motor or the like, is adapted to rotatably oscillate the objective lens 51 and the mirror member 52 about the longitudinal axis of the optical paths 21 and 61 through the rotational holding member 55, so that the object surrounding the rotational holding member 55 can be cylindrically scanned. In this case, the rotational oscillation can be performed within a range defined by torsional elasticity limits of the optical paths 21 and 61, which lead to eliminate the necessity of providing a mechanical break point halfway through the optical paths 21 and 61, as in conventional structures. Therefore, it is possible to suppress optical losses and reflection ghosts caused by such a mechanical break point, thereby achieving rotational scanning with higher reliability and lower costs.

The sheath 57, which is formed of a single hollow cylindrical member that can be made of a hard material, such as metal or plastic, or a bendable and flexible material. The sheath 57, supports the rotational holding member 55 inside thereof so that it can be rotated. The sheath holding member 58 fixes the sheath 57 for restricting the rotational movement of the sheath 57.

In this embodiment, the two optical paths 21 and 61 are housed in the single sheath 57, which facilitates handling of the probe 50. Further, the rotational oscillation mechanism 56 is adapted to integrally rotate and oscillate the respective optical paths 21 and 61 with respect to the sheath 57, thereby suppressing influences on the object during rotational scanning. Further, the object is free of any load, thereby realizing smooth rotational scanning.

In this embodiment, similarly to the second and third embodiments, a fixing holding member 25 is installed halfway through the optical paths 21 and 61 for restricting the torsional range thereof. Installation of the fixing holding member 25 can restrict the areas of the torsion portions 21a and 61a which are torsionally oscillated, out of the entire optical paths 21 and 61. This reduces variation of the elasticity limit due to bending or attitude changes of the optical paths 21 and 61, thereby making it easy to set a maximum value of the amount of torsional rotation.

Industrial Applicability

The present invention is industrially available, since it provides an optical rotary probe with a simple structure and with excellent reliability.

The invention claimed is:

1. An optical rotary probe for directing light to an object to be measured and receiving light returned from the object to be measured, the optical rotary probe comprising:
an optical waveguide for transmitting light from a light source;
a mirror member for reflecting the light transmitted through the optical waveguide;
a rotational holding member for housing a tip end portion of the optical waveguide and the mirror member; and
a rotational oscillation mechanism for rotatably oscillating the mirror member and the tip end portion of the optical waveguide about a longitudinal axis of the optical waveguide through the rotational holding member;
wherein the rotational oscillation mechanism is adapted to perform the rotational oscillation within a range defined by a torsional elasticity limit of the optical waveguide.

2. The optical rotary probe according to claim 1, wherein a fixing holding member for restricting a torsional range is provided halfway through the optical waveguide.

3. The optical rotary probe according to claim 1, wherein a sag is provided in the torsionally oscillating portion of the optical waveguide.

4. The optical rotary probe according to claim 1, wherein measurement is performed within a constant speed interval of the torsional oscillation while no measurement is performed within a non-constant speed interval.

5. The optical rotary probe according to claim 1, wherein a second optical waveguide is further provided for transmitting return light from the object to be measured.

6. The optical rotary probe according to claim 5, wherein the respective optical waveguides are housed in a single bendable flexible member.

7. The optical rotary probe according to claim 6, wherein the rotational oscillation mechanism is adapted to integrally rotatably oscillate the respective optical waveguides with respect to the bendable flexible member.

8. The optical rotary probe according to claim 1, further comprising a detector for detecting a rotational angle of the rotational holding member or the rotational oscillation mechanism.

* * * * *